United States Patent
Bonillas Vaca (10) Patent No.: US 11,317,972 B2
(45) Date of Patent: May 3, 2022

(54) METHOD FOR VIRTUAL DEVICE POSITIONING ON SKIN SURFACE IN 3D MEDICAL IMAGE DATA

(71) Applicant: Canon U.S.A., Inc., Melville, NY (US)

(72) Inventor: Antonio Bonillas Vaca, Boston, MA (US)

(73) Assignee: Canon U.S.A., Inc., Melville, NY (US)

( * ) Notice: Subject to any disclaimer, the term of this patent is extended or adjusted under 35 U.S.C. 154(b) by 509 days.

(21) Appl. No.: 16/355,023

(22) Filed: Mar. 15, 2019

(65) Prior Publication Data
US 2019/0282301 A1    Sep. 19, 2019

Related U.S. Application Data

(60) Provisional application No. 62/644,496, filed on Mar. 17, 2018.

(51) Int. Cl.
| | |
|---|---|
| A61B 34/10 | (2016.01) |
| A61B 34/20 | (2016.01) |
| A61B 17/00 | (2006.01) |
| G06T 15/08 | (2011.01) |
| A61B 90/00 | (2016.01) |
| A61B 34/30 | (2016.01) |
| G06T 7/00 | (2017.01) |
| A61B 18/00 | (2006.01) |

(52) U.S. Cl.
CPC ........ *A61B 34/10* (2016.02); *A61B 17/00234* (2013.01); *A61B 34/20* (2016.02);
(Continued)

(58) Field of Classification Search
CPC ........ A61B 17/00234; A61B 2017/003; A61B 2018/00577; A61B 2034/102; A61B 2034/107; A61B 2034/2059; A61B 2090/374; A61B 2090/3762; A61B 2090/378; A61B 34/10; A61B 34/20; A61B 34/25; A61B 34/30; A61B 90/11;
(Continued)

(56) References Cited

U.S. PATENT DOCUMENTS

| | | | |
|---|---|---|---|
| 6,671,538 B1 * | 12/2003 | Ehnholm | A61B 90/10 382/131 |
| 6,782,288 B2 | 8/2004 | Truwit et al. | |

(Continued)

FOREIGN PATENT DOCUMENTS

| | | |
|---|---|---|
| JP | 2005-136981 A | 5/2005 |
| JP | 2017023516 A | 2/2017 |

(Continued)

OTHER PUBLICATIONS

Peng Song, et al., Grasp planning via hand-object geometric fitting. The Visual Computer, Feb. 2018, vol. 34, Issue 2, pp. 257-270, also published online Nov. 7, 2016, Springer-Verlag, Berlin Heidelberg, Germany.

*Primary Examiner* — Mark D Remaly
(74) *Attorney, Agent, or Firm* — Canon U.S.A., Inc. IP Division (57) ABSTRACT

Systems, methods, and computer-readable media are provided. Some embodiments include image guidance software comprising an algorithm for registering the virtual device model to the image space automatically, approximating the most likely configuration of the device on the skin surface before the actual device is placed on the patient. The virtual model of the device and its reachable area are overlaid on the planning image data, in order to visualize and quantify the reachability of the target.

12 Claims, 6 Drawing Sheets

(52) U.S. Cl.
CPC .............. *A61B 34/30* (2016.02); *A61B 90/37* (2016.02); *G06T 15/08* (2013.01); *A61B 2017/003* (2013.01); *A61B 2018/00577* (2013.01); *A61B 2034/107* (2016.02); *A61B 2090/374* (2016.02); *A61B 2090/378* (2016.02); *A61B 2090/3762* (2016.02); *G06T 7/0012* (2013.01); *G06T 2207/30004* (2013.01); *G06T 2210/41* (2013.01)

(58) Field of Classification Search
CPC ............... A61B 90/37; G06T 15/08; G06T 2207/10081; G06T 2207/10088; G06T 2207/30004; G06T 2207/30021; G06T 2210/41; G06T 7/0012; G06T 7/75
See application file for complete search history.

(56) References Cited

U.S. PATENT DOCUMENTS

| | | | |
|---|---|---|---|
| 9,222,996 | B2 | 12/2015 | Fujimoto et al. |
| 9,408,627 | B2 | 8/2016 | Sahni |
| 2008/0091101 | A1 | 4/2008 | Velusamy |
| 2008/0234700 | A1 | 9/2008 | Trovato et al. |
| 2009/0131783 | A1 | 5/2009 | Jenkins et al. |
| 2011/0046935 | A1 | 2/2011 | Sugaya |
| 2013/0274778 | A1 | 10/2013 | Mercier et al. |
| 2014/0303662 | A1 | 10/2014 | Aoyagi |
| 2015/0148660 | A1 | 5/2015 | Weiss et al. |
| 2016/0008082 | A1 | 1/2016 | Takagi |
| 2016/0074063 | A1 | 3/2016 | Arimitsu et al. |
| 2016/0166355 | A1 | 6/2016 | Farah |
| 2016/0310215 | A1* | 10/2016 | Palma .................... A61B 34/10 |
| 2017/0000581 | A1 | 1/2017 | Tokuda et al. |
| 2018/0228568 | A1 | 8/2018 | Kato et al. |

FOREIGN PATENT DOCUMENTS

| | | |
|---|---|---|
| JP | 2017512523 A | 5/2017 |
| JP | 2017530758 A | 10/2017 |
| JP | 2018529399 A | 10/2018 |
| WO | 2009067654 A1 | 5/2009 |
| WO | 2014041579 A1 | 3/2014 |
| WO | 2017003453 A1 | 1/2017 |

* cited by examiner

METHOD FOR VIRTUAL DEVICE POSITIONING ON SKIN SURFACE IN 3D MEDICAL IMAGE DATA

CROSS-REFERENCE TO RELATED APPLICATIONS

This application is a non-provisional United States patent application that claims the benefit of provisional U.S. Patent Application No. 62/644,496 filed on Mar. 17, 2018. Provisional U.S. Patent Application No. 62/644,496 is hereby incorporated by reference herein in its entirety.

FIELD OF THE DISCLOSURE

The present disclosure relates generally to medical imaging and, more particularly to systems, methods, and devices for planning and carrying out minimally invasive procedures using external devices for needle guidance.

BACKGROUND INFORMATION

Medical images assist physicians in planning, performing, and post-operative analysis of a procedure. Some imaging modalities that are useful include ultrasound imaging, computed tomography (CT), and magnetic resonance imaging (MRI). Medical images can also be used to assist in navigating various instruments relative to the patient while performing a procedure. It is important to accurately place a device on the patient relative to the treatment area.

During planning for minimally invasive image-guided needle interventions (biopsy, ablation therapy, etc.), a target lesion or anatomy is usually identified in medical images of modalities such CT, MRI, etc. An insertion point on the skin surface is also usually identified to determine the needle trajectory. The possible trajectories depend on the geometry and steerability of the needle. To aid in directing the needle along the planned trajectory a guidance device may be used, positioned on or near the patient skin. The device geometry plus the length and geometry of the needle will place constraints on the reachable area, so a mental picture is formed based on knowledge of the device, experience and measurements on the image data to determine whether the target is reachable from the chosen insertion point. During the procedure the device is placed on the patient and new images are acquired, on which the device can be identified and registered to the image space. It can then be confirmed whether the target is reachable.

U.S. Pat. No. 6,782,288 describes a device with a needle guide pivoting about a pivot point and the method to align the guide with the desired needle trajectory using an imaging system and related software. U.S. Pat. No. 9,408,627 describes a whole-body stereotactic needle placement device consisting of a circular base plate, semicircular rotating arc and needle guide, and the related image guidance software. However, in conventional systems such as described above, there is no provision for simulating the device placement in the imaging software during planning for evaluating target reachability. Thus, before the needle guidance device is placed on the patient, imaged and registered to the image space, it is difficult to be certain that the target point is reachable from the chosen insertion point using the device.

SUMMARY OF EXEMPLARY EMBODIMENTS

It would therefore be desirable to provide a system and method that simulates device placement in the imaging software during planning for evaluating target reachability and aiding in optimal device placement.

Systems, methods, and computer-readable media for simulating the device placement during planning in order to visualize and quantify the reachability of the target are disclosed. According to embodiments of this disclosure, medical image data is obtained from some imaging system (CT, MRI, etc.). Some embodiments include an image guidance system that allows defining the needle trajectory by setting target and insertion point locations, and that includes a 3D model representation of the physical guidance device and the needle or instrument to be used in the procedure.

Some embodiments include image guidance software comprising an algorithm for registering the virtual device model to the image space automatically, approximating the possible configurations of the device on the skin surface before the actual device is placed on the patient, and suggesting recommended positioning. The virtual model of the device and its reachable area, based on the needle geometry, are overlaid on the planning image data, in order to visualize and quantify the reachability of the target.

According to some embodiments, the systems and methods disclosed herein use medical image data as input. Moreover, in some embodiments, the systems and methods herein use as input a needle guide device model representation, including: bottom surface (plane and foot print); reachable area of device; and geometrical relationship between bottom surface and reachable area. In some embodiments, the systems and methods herein use image guidance software that allows: visualizing medical image data; defining skin entry point and target; and computing best bottom surface position and orientation for the needle guide device. According to some embodiments, determining the needle guide device orientation includes: pivoting the device model around a device center relative to the skin entry point; computing a metric related to correspondence between skin and bottom surface; and iterating the above steps to optimize the metric. In some embodiments, the device center relative to the skin entry point can have multiple configurations and an optimal configuration is determined by computing a metric for reachability and iterating to optimize the metric. Moreover, some embodiments include displaying the reachable area of the device on the medical image data by using the known geometrical relationship and the computed device to image registration. Furthermore, some embodiments include computing the best bottom surface orientation by: pivoting the device model around the skin entry point; defining the axis on the device model for computation; computing metric related to correspondence between the skin plane and bottom surface of the needle guide device; iterating the computing step to optimize the metric; and repeating the above steps for another axis, in accordance with the disclosure.

Further features of the present disclosure will become apparent from the following description of exemplary embodiments with reference to the attached drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the present disclosure and, together with the description, serve to explain the principles of the present disclosure.

DETAILED DESCRIPTION OF EXEMPLARY EMBODIMENTS

Figure 1:
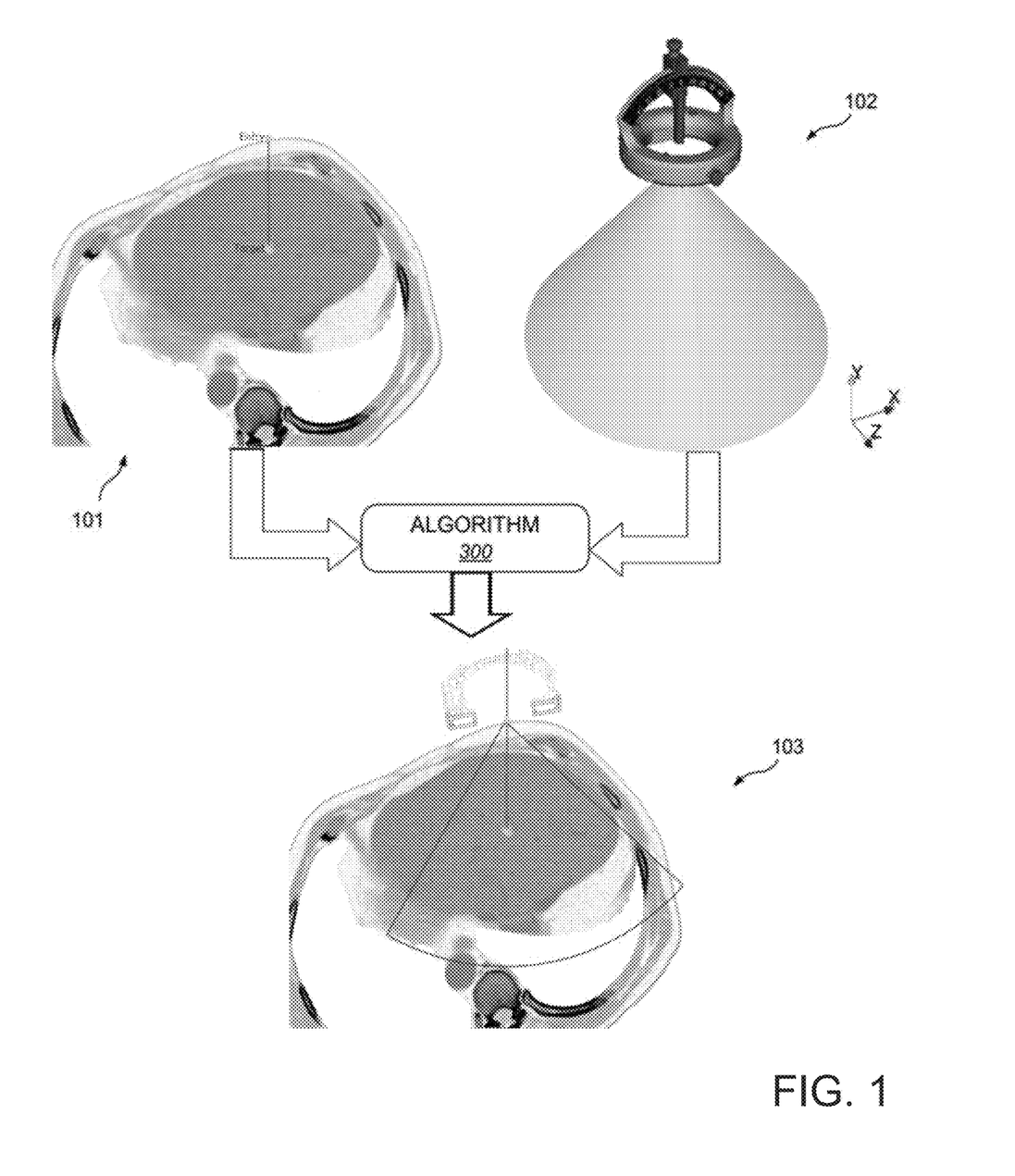
FIG. 1 shows a medical image presented on an example graphical user interface, a device model of an example needle guidance device, and an image illustrating the device model overlaid on the medical image, in accordance with some embodiments.

Exemplary embodiments are described below with reference to the drawings. FIG. 1 illustrates planning image data 101, a device model 102, and registered device model 103 overlaid on the planning image data 101 after applying an algorithm 300. The algorithm 300 is described in detail below with reference to FIG. 3. In some embodiments, image guidance software running on a computing system receives the planning image data 101 and, using the device model 102, determines the orientation of the registered device model 103 by executing the algorithm 300.

In some embodiments, the planning image data 101 is medical image data obtained from some imaging system (CT, MRI, etc.). The image guidance software allows for defining a needle trajectory by setting target and insertion point locations. Additionally, the image guidance software may calculate an insertion depth based on the needle trajectory and the planning image data 101. In some embodiments, the image guidance software includes the device model 102. The device model 102 is a 3D model representation of the physical guidance device to be used in a procedure. The device model 102 can be overlaid or otherwise represented in conjunction with image data of a subject, for example, to provide a surface model of virtual representation of a physical guidance device either placed, or to be placed, on a surface of a patient or other image subject. The physical guidance device may be any suitable device for guiding a needle, probe or other medical device during preparation or performance of the procedure. The needle may be any suitable size or length needle for the procedure. In some embodiments data corresponding to each needle of a plurality of needles or other medical device(s) is/are stored in the computing system as respective device models included in the image guidance software.

In some embodiments, the image guidance software contains the algorithm 300, described in this disclosure, for registering the virtual device model 102 to the image space automatically. The algorithm 300 approximates the most likely configuration of the device on the skin surface before the actual device is placed on the patient. The registered device model 103 and its reachable area are overlaid on the planning image data 101, in order to visualize and quantify the reachability of the target.

Figure 3:
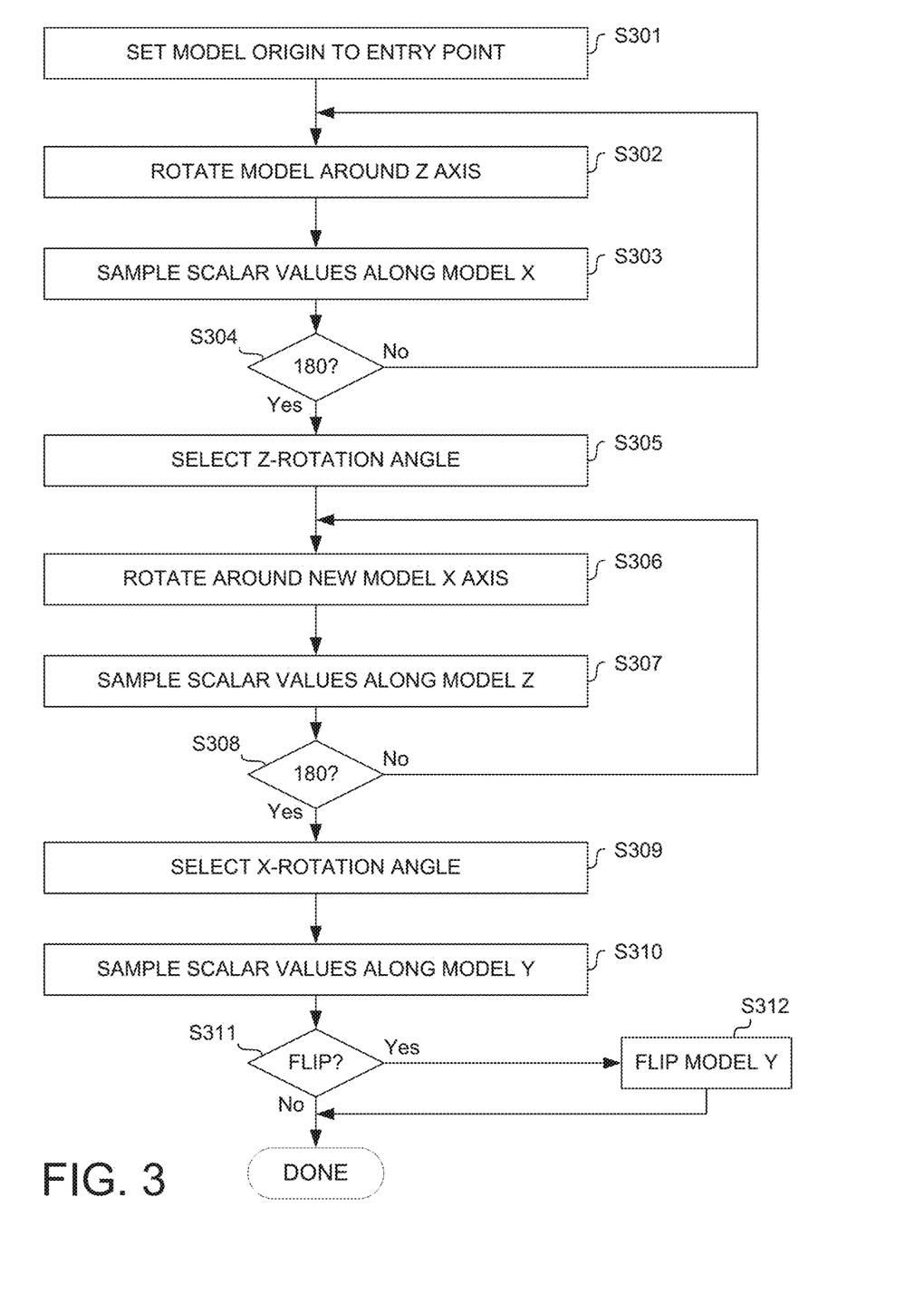
FIG. 3 is a flow diagram illustrating a process of determining an optimal orientation for evaluating target reachability in accordance with some embodiments.

The algorithm 300 performs the process illustrated in FIG. 3 to determine an optimal orientation for evaluating target reachability. As described in more detail below, the planned insertion point is used to determine the position of the device origin and serves as a pivot for determining the approximate orientation on the patient so that the device model 102 surface adapts to the skin surface.

According to FIG. 3, the device model 102 is rotated about an arbitrary axis passing through the insertion point and samples of the underlying image data values are collected for different angle positions at a set of points that correspond to the device model 102 surface at a geometry that is perpendicular to the rotation axis. A metric to be optimized is calculated for the point sample values at each angle, such as the range, gradient or a combination thereof, that can be specific to the imaging modality, and the optimal value determines the first device model rotation angle.

Then, the resulting device model is subsequently rotated about a second axis that is orthogonal to the first rotation axis and parallel to the surface of the device model after the first axis rotation, and sampled the same way at a set of points on the device model surface at a geometry that is perpendicular to the second rotation axis. The optimal value determines the second rotation angle.

The resulting device model after applying the two rotations is expected to roughly conform to the patient skin surface orientation, but additional iterations can be performed using new axes of the resulting device model. A last step is to check whether the device model may be flipped 180 degrees, for which samples of image data values on either side of the resulting surface plane are taken, and the device model flipped if necessary. The algorithm 300 is further described below with reference to FIG. 3.

Figure 2A:
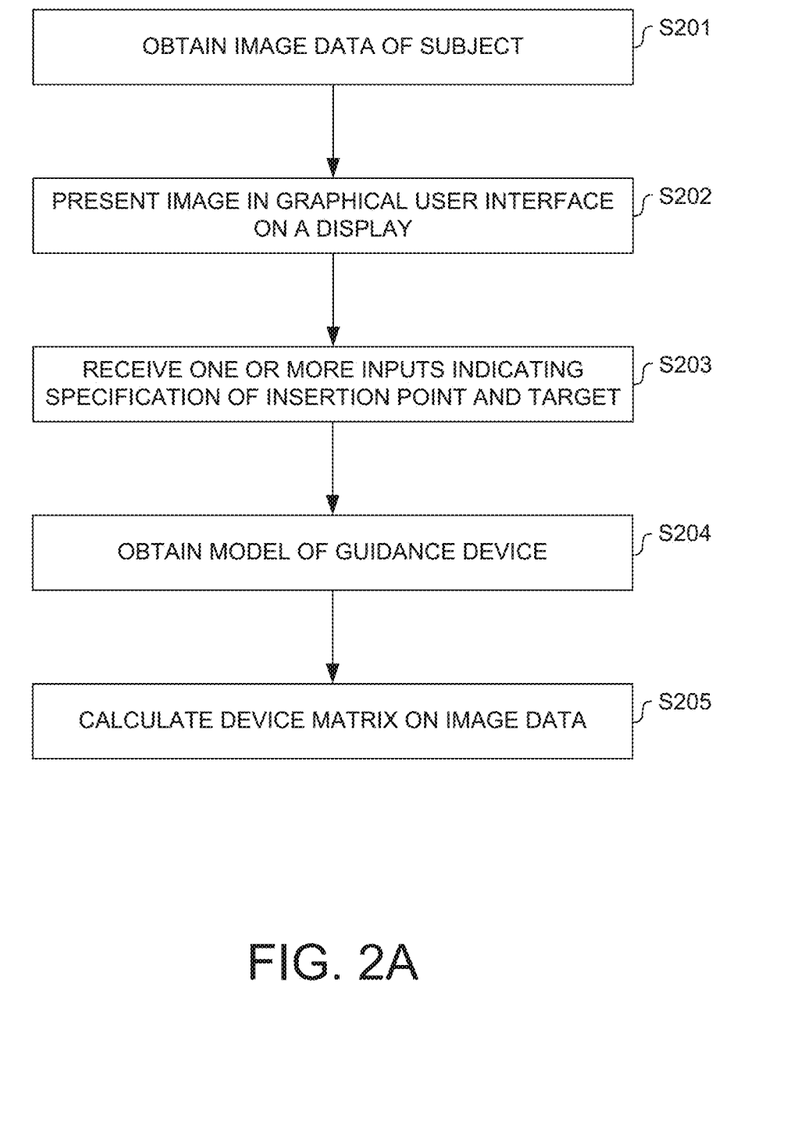
FIG. 2A is a flow diagram illustrating processing of image and device model data in accordance with some embodiments.
Figure 2B:
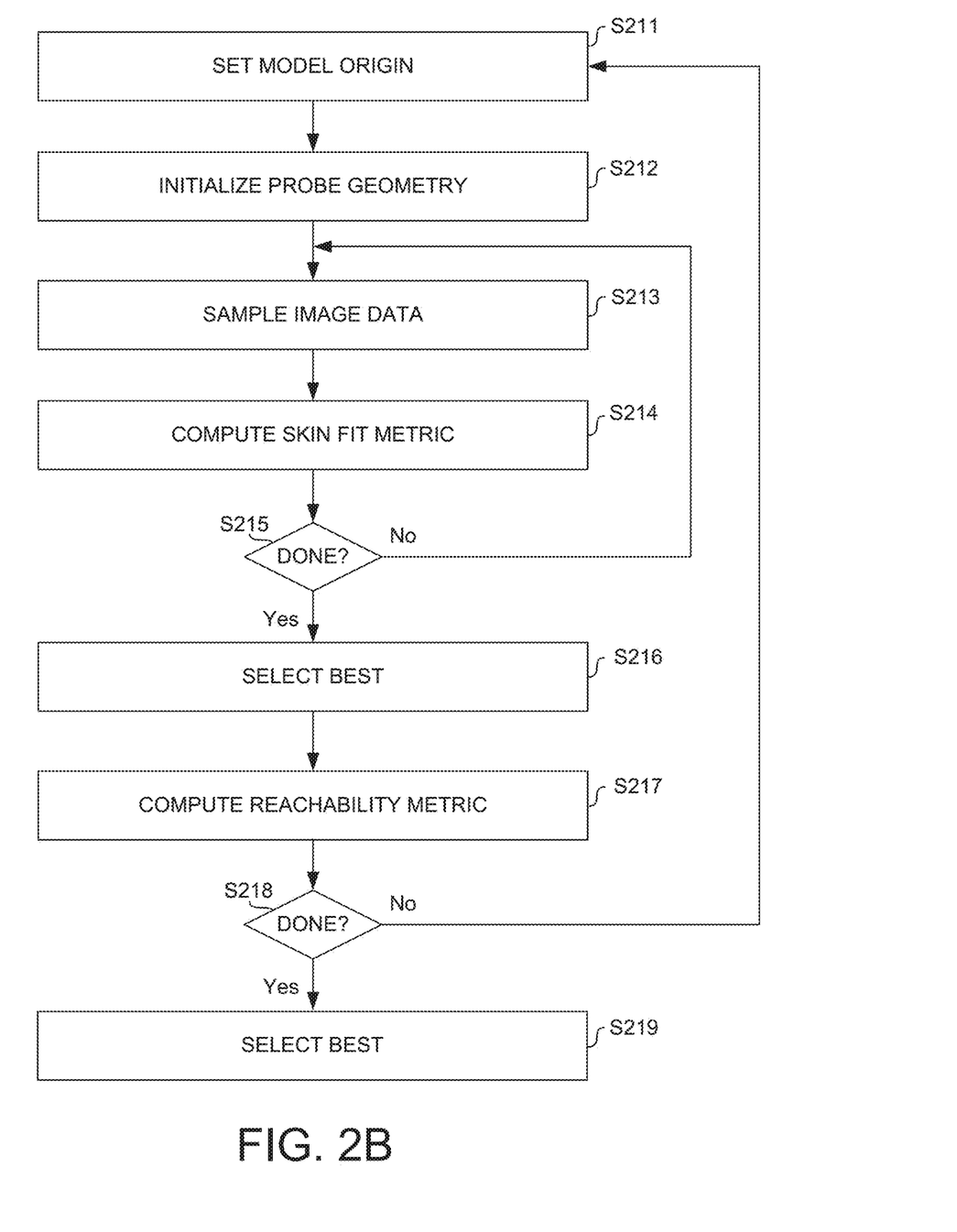
FIG. 2B is a flow diagram illustrating a general process for calculating an optimal device position and orientation matrix from the image and device model data.

FIGS. 2A and 2B are flow diagrams illustrating examples of operations at a computing system running image guidance software. In some embodiments, the image guidance software running on the computing system 500 described with reference to FIG. 5 performs the operations illustrated in FIGS. 2A and 2B based on information associated with pre-procedure planning According to some embodiments, the planning image data 101 of FIG. 1 is medical image data obtained in step S201 of FIG. 2A.

In step S201, the computing system 500 obtains image data of a subject. For example, the image data may be medical image data of a patient's anatomy. In some embodiments, the image data includes MRI data. For example, while a patient is in the gantry of an MRI scanner, the MRI scanner scans at least a portion of the patient's body. Based on the scan, the MRI scanner generates an image of the patient's anatomy and the MRI system 404 sends 3D image data of the patient's anatomy to the computing system 500. In some embodiments, the image data includes CT data. For example, a CT scan of a portion of a patient's body may be taken and the image data generated based on the CT scan. After the image data is generated, the imaging system sends the image data to the computing system 500.

In some embodiments, the computing system 500 obtains the image data as a file from a source other than the imaging system that generated the image data. For example, the computing system 500 may read or retrieve the file from a storage device, such as a USB flash drive connected to the computing system 500, or any other suitable storage medium accessible to the computing system 500. In some embodiments, the computing system 500 obtains the image data from a computing system that transmits the image data file over a network, such as a LAN, WAN, other suitable network, or combination of networks.

The image guidance software executing on the computing system 500 thus obtains the image data at the computing system 500 from, for example, the imaging system which generated the image data, or from a storage medium, or from another computing system over a network.

In step S202, the image guidance software executing on the computing system 500 presents the image data, obtained in step S201, in a GUI on a display. In some embodiments, the computing system 500 includes a display, and the image data is presented in a GUI on the display of the computing system 500. In some embodiments, the display is an output device and the image guidance software executing on the computing system 500 outputs the image data to the display via the I/O interface 504. In some embodiments, step S202 includes presentation of a medical image in a GUI, the medical image including a 3D representation of the patient's anatomy. The medical image presented in the GUI may be used as a planning image for pre-procedure planning of a medical procedure. For example, the image guidance software executing on the computing system 500 provides a GUI including interface elements and features which enable a user, such as a doctor, to provide inputs via the GUI to specify one or more location(s) on the medical image presented in the GUI. In some embodiments, the GUI displays a section of the planning image along any plane and allows the physician to specify targets and skin entry points. Accordingly, a physician can define a trajectory of needle placement by specifying the targets and skin entry point on the planning image.

In step S203, the computing system 500 receives one or more input(s) indicating the specification of an insertion point and a target on the medical image. In some embodiments, step S203 includes receiving the input(s) while the medical image is presented in the GUI on the display. The input(s) may be received in any suitable manner. By way of example and not by way of limitation, a user may provide one or more input(s) specifying the insertion point and the target on the medical image by one or more of the following: touching a touch sensitive display with a finger, stylus, or other tool; controlling a cursor with a mouse or touchpad; pressing a key, button, or other input structure; manipulating or selecting one or more interface elements included in the GUI; another technique for providing an input; or a combination of two or more of these. The planned insertion point is a skin entry point at which a needle is to be inserted into the patient's body. The target is the location, spot or area to be treated and/or the anatomy to be accessed. The trajectory of needle placement is defined by connecting the planned insertion point and the target.

In step S204, the computing system 500 obtains a device model of the physical guidance device. The device model is typically coded in software, for example using a computer aided design (CAD) software program, in advance based on an engineering specification of the geometry and function of the various components of particular physical guidance device to be used on the subject. For example, as shown in FIG. 1, the physical guidance device may be a needle guidance device which may be rotated around a rotation axis perpendicular to a subject (such as a patient) and having an arc shaped handle portion which allows a needle guide to be canted by an angle off the aforementioned rotation axis to allow a needle, or alternatively a medical probe or other medical instrument, to be guided along the cant angle into the subject. The cant angle can be determined, for example, by determining a straight line from a needle entry point and a target location representation in the image scan of the subject, for example, as illustrated in the planning image data 101 shown in FIG. 1.

In step S205, the computing system 500 calculates a device matrix which specifies a location for placement of the physical guidance device on the subject. In particular, for example, the computing system 500 may calculate a virtual representation of the physical guidance device on a surface of the subject as shown in scan data or other image data. Further, step S205 may specify how the physical guidance device can be mounted on the surface of the subject so rest in stable manner on the surface of the subject. Moreover, step S205 can determine how to angle the base of the physical guidance device, for example the needle insertion device 102 as shown in FIG. 1, so that contact is provided over either all or a large portion of the base of the physical guidance device so as to provide a stable mounting on the surface of a patient or other imaging subject. Moreover, step S205 may compute a reachability metric which indicates a range through which a medical device may be guided into the subject using the physical guidance device, and moreover, may compute an indication of whether there is ample additional range (e.g. headroom) for usage of the medical device to be guided in the subject. A virtual representation of the physical guidance device as it would appear on the surface of the subject may be provided, for example displayed, superimposed on the image data. Furthermore, a plurality of potential mounting locations may be determined, and then a best fit identified for a user, or alternatively, the user may be allowed to select a best fit based on the user's medical knowledge. Additional details of a particular implementation of step S205 are provided below with reference to FIG. 2B.

Figure 5:
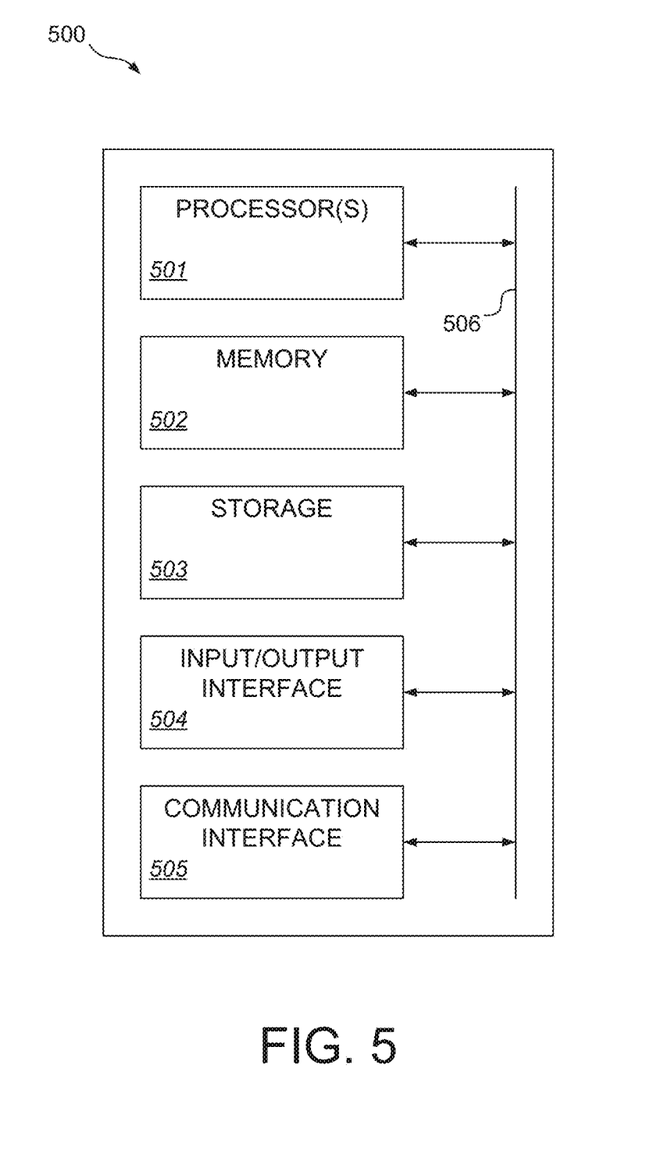
FIG. 5 illustrates an example computing system in accordance with some embodiments.

Referring now to FIG. 2B there is shown a flow diagram illustrating a general process that may be performed by the computing system 500 of FIG. 5 to calculate an optimal device position and orientation matrix from the image and device model data. The process of FIG. 2B is useful, for example, for performing the processing of step S205 of FIG. 2A. In step S211, the computing system 500 obtains image data of a subject, for example, by reading previously prepared scan data of the subject from storage 503. In step S212, the computing system 500 loads a software model of the physical guidance device from storage 503 into memory 502. Once the software model of the physical guidance device is loaded into memory 502, the computing system 500 links the software model of the physical guidance device to geometry of a software model of the subject based on the image data of the subject. This may include, for example, preparing a virtual representation of the physical guidance device superimposed on the scan data, and may also include a providing an illustration of the virtual representation of the physical guidance device superimposed on an illustration of the scan data, for example, on a display device, so that the physician, medical provider, or other user can see how the physical guidance device would appear if placed on the subject (e.g. a patient).

In step S213, the computing system 500 samples scalar values in the scan data along a sample line selected in the scan data. The sample line can be, for example, a straight line or curvilinear path through a point on the subject that lies beneath the virtual representation of the physical guidance device as linked to the geometry of the software model of the subject. As an example, any point beneath the virtual representation of the physical guidance device can be used, although it is frequently useful to select a point that is centered (or axially centered) beneath the software model of the physical guidance device, especially if the physical guidance device has rotational symmetry and/or is rotatable around an axis of rotation of a base of the physical guidance device. Thus, for example, a sample line can be selected that runs through a point of intersection of the axis of rotation of the base of the physical guidance device and a surface (e.g. skin surface) of the subject as indicated in the virtual representation of the physical guidance device superimposed on the scan data. A plurality of points along the line may be selected. For each such point, the scan data is sampled. The sampled data includes data representing a small region surrounding the point, for example, in a small sphere centered on (or otherwise including) the point. Accordingly, the sampled data of such a point includes data representing locations in a neighborhood around the sample point, and accordingly, mathematical attributes, such the gradient derivative of data values in the neighborhood, of the sampled data of the point can be used to determine attributes of the point. An example of such is computing a gradient derivative (commonly called the gradient) $\nabla f$ of values f of the sample data in the neighborhood around the sample point. Further examples of step S213 are provided below in steps S303, S307, and S310 with respect to FIG. 3.

In step S214, the computing system 500 determines a skin fit metric of the virtual representation of the physical guidance device superimposed on the scan data. For example, the computing system 500 may calculate the gradient $\nabla f$ in a respective neighborhood of each of the sampled points along the sample line discussed above with respect to step S213. If the gradient $\nabla f$ is a constant (such as zero) or close thereto throughout such a neighborhood, then the computing system 500 determines that the sample point most likely lies in the air over or adjacent to the subject, but does not lie on the surface of or inside the subject, as values of scan data in air typically are very close in value because the density, temperature, and other physical parameters detectable by the scan do not change much in the air around the subject. That is, most values of scan data that come from points in the air around the subject are typically about the same in value, and hence result in little change in the gradient $\nabla f$. The value of the gradient $\nabla f$ may be approximately zero throughout a neighborhood around a sample point in the air. If the gradient $\nabla f$ includes a sharp change in values along a line or plane in the neighborhood, then the computing system 500 determines that the sample point most likely lies or very close to the surface of the subject, with the sharp change in values at such line or plane occurring at the surface of the subject. If the gradient $\nabla f$ includes small changes in values in the neighborhood but does not include a sharp change in values, then the computing system 500 determines that the sample point most likely lies inside the patient, with the small changes values of the gradient representing changes in the nature of the tissues of the subject throughout such neighborhood, such as for example, changes in value of the gradient $\nabla f$ which occur at membranes or blood vessels in muscle or deep portions of the skin of the subject. For each such point along the sample line, the computing system 500 determines whether the sample point likely represents a point on or very close to the surface of the subject. The number of sample points on the sample line that lie on or very close to the surface of the subject is counted by the computing system 500. If that count meets or exceeds a preselected value (such three) then the computing system 500 may determine that the virtual representation of the physical guidance device lies on the surface of the subject as represented by the scan data.

In step S215, the computing system 500 decides whether further calculation is needed to locate a virtual placement of the physical guidance device on the surface of the subject. For example, if the count of step S214 meets or exceeds the preselected value (e.g. three) then the computing system 500 may determine that further calculation is not needed to locate a virtual placement of the physical guidance device on the surface of the subject (YES in step S215), whereas if the count of step S214 does not meet or exceed the preselected value (e.g. the count is two or less) then the computing system 500 may determine that further calculation is needed to locate a virtual placement of the physical guidance device on the surface of the subject (NO in step S215). However, preferably the computing system is programmed to perform steps S213 and S214 a plurality of times, so that NO is determined in step S215 a plurality of times until a plurality of virtual placement of the physical guidance device on the surface of the subject are found after iteration, as next addressed. If the determination is NO in step S215, then processing returns to step S213 to perform an iteration of the processing of steps S213 and S214 along a newly selected line in the scan data. The newly selected sample line may be a straight line or curvilinear path that is obtained by rotating prior sample line along the rotation axis of the virtual representation of the physical guidance device, which is useful for example if at least one of the sample points of the prior sample line has been determined to lie on or very close to the surface of the subject. Alternatively, and particularly if none of the sample points of the prior sample line have been determined to lie on or very close to the surface of the subject, the computing system 500 may determine the newly selected sample line by selecting a line through the sample data that does not intersect the prior sample line, for example, by shifting or shifting and rotating the prior sample line. If the determination is YES in step S215, the computing system 500, the processing proceeds to step S216.

In step S216, the computing system 500 selects a best fit or optimal fit among the virtual placements of the physical guidance device provided by the prior processing steps S211, S212, S213, S214, and S215 with iteration. For example, in one embodiment, the computing system 500 compares the virtual placements of the physical guidance device and determine the best fit or optimal fit as being the virtual placement having the most sample points that are on or very close to the surface of the subject. In another embodiment, the computing system 500 computes a distance to the skin of the subject for each of the virtual placements of the physical guidance device provided by the prior processing steps S211, S212, S213, S214, and S215. A virtual placement that is closest to the skin is selected as the best fit or optimal fit. Processing then proceeds to step S217.

In step S217, the computing system 500 computes a reachability metric for the selected best fit or optimal fit. In particular, the computing system 500 determines whether a candidate target point inside the subject (for example a location that is to receive the load of an injection or that is to receive ablation) would be within reachable range (reachable area) of a needle or medical device to be guided by the physical guidance device. Moreover, the computing system 500 may calculate how close the candidate target point is to the boundary of the reachable range. This is particularly valuable as sufficient headroom for usage medical device (e.g. needle or ablation probe) is valuable for the physician, medical provider, or other user.

In step S218, the computing system 500 determines whether further iterations of the prior processing steps S211, S212, S213, S214, S215, S216, and S217 would likely be useful. For example, if the boundary of the reachable range is close to the candidate target point, then further iteration of prior processing steps S211, S212, S213, S214, S215, S216, and S217 would be useful so that virtual placement of the physical guidance device can be found having the candidate target point at (or near to) a center of the reachable range, so as to provide ample headroom for the physician, medical provider, or other user. If further iteration would likely be useful (NO in step S218), the processing returns to step S211, otherwise (YES in step S218) processing continues at step S219.

In step S219, the computing system 500 selects the best or optimal virtual placement of the physical guidance device. The best or optimal virtual placement of the physical guidance device can be displayed to the physician, medical provider, or other user. Alternatively, the physician, medical provider, or other user can be shown each of the virtual placements of the physical guidance device provided out of step S218, and then select the best virtual placement based on medical knowledge or skill. According to an aspect of the present embodiment, the above described processing of FIGS. 2A and/or 2B can be performed during a medical procedure. However, according to another aspect of the present embodiment, the above described processing of FIGS. 2A and/or 2B can be performed before (e.g., well before) a medical procedure that uses the physical guidance device on the subject, for example, by performing the scan of the subject at one time, thereafter performing the processing of FIGS. 2A and/or 2B, and thereafter (and potentially at a later time or date) performing an actual medical procedure using the physical guidance device by placement of the physical guidance device at the best or optimal placement as determined by the processing of FIGS. 2A and/or 2B. Such aspects of the present embodiment are highly useful, for example, because the physician, medical provider, or other user can determine well ahead of time where the physical guidance device can optimally be placed, and accordingly, can well plan the medical procedure well ahead of time.

In some embodiments, one or both of the insertion point and the target is/are set without the medical image being presented in a GUI on a display. For example, the insertion point or the target may be set based on an input representing a point in a coordinate system corresponding to the planning image data 101. In some embodiments, the insertion point and/or target is/are calculated based on the planning image data 101.

After the insertion point and target are set, the image guidance software executing on the computing system 500 may send the defined trajectory to a robot control server, such as described with reference to FIG. 4. In some embodiments, information indicating the target and the planned insertion point are sent as part of the processing of either or both of FIG. 2A and FIG. 2B. For example, according to some embodiments, the robot control server uses the target and insertion point information to determine the trajectory at the robot control server. In some embodiments, the image guidance software determines the trajectory of needle placement by connecting the planned insertion point and the target. Then, the image guidance software transfers to the robot control server the defined trajectory.

In some embodiments, the image guidance software executing on the computing system 500 presents a 3D image with the defined trajectory in the GUI on the display. For example, the computing system 500 may present a re-sliced 3D image with plane along a defined trajectory in the GUI on the display once the trajectory has been defined. The image guidance software may re-slice the 3D image with a plane along the trajectory so that the physician can find any critical structures and obstacles around the path. By way of example, the planning image data 101 of FIG. 1 may be presented as a medical image on a graphical user interface of the image guidance software. The image may include a 3D representation of patient anatomy and information identifying a planned trajectory and target, and the image may be sliced with plane along the defined trajectory.

FIG. 3 is a flow diagram illustrating a process of determining an optimal orientation for evaluating target reachability in accordance with some embodiments.

In step S301, the computing system 500 sets the device model 102 origin to the insertion point. For example, the device model 102 origin may be set to the insertion point shown in the planning image data 101. In some embodiments, the computing system 500 sets the device model 102 origin to the insertion point specified/set in a manner described with reference to FIGS. 2A and 2B. The planned insertion point is used to determine the position of the device origin and serves as a pivot for determining the approximate orientation on the patient so that the device model 102 surface adapts to the skin surface. The device model 102 surface, i.e., the base plane of the device model 102, illustrated in FIG. 1 is parallel to the XZ plane shown in FIG. 1.

In other embodiments, the pivot point of the device may be at a fixed distance from the insertion point, depending on the geometry of the device, and multiple device origin locations can be evaluated.

In step S302, the computing system 500 rotates the device model 102 around an arbitrary axis. For example, the computing system 500 may rotate the device model 102 around the Z axis shown in FIG. 1. The device model 102 is rotated about the arbitrary axis passing through the insertion point.

In step S303, the computing system 500 samples scalar values along the X axis. In step S304, the computing system 500 determines whether the device model 102 has been rotated 180 degrees. If not (No in step S304), the process returns to step S302 and the process S302-S304 is repeated. Accordingly, for each angle as the device model 102 is rotated, samples of the underlying image data values are collected for different angle positions at a set of points that correspond to the device model 102 surface at a geometry that is perpendicular to the rotation axis. The amount of sample scalar values collected is based on the desired resolution. For example, in some embodiments the process S302-S304 is repeated for every one degree for a total of 180 sample scalar values. For each angle, multiple points in the image are sampled, each point corresponding to a voxel of the image. A sample scalar value is obtained along the X axis for each incremental degree of rotation around the Z axis. When the computing system 500 determines that the device model 102 has been rotated 180 degrees and all sample scalar values have been collected for each sampled angle (Yes in step S304), then the process advances to step S305.

In step S305, a metric to be optimized is calculated for the point sample values at each angle, such as the range, gradient or a combination thereof, that can be specific to the imaging modality, and the optimal value determines the first device model rotation angle. The device model 102 rotation angle selected in step S305 may be the angle which corresponds to a sampled scalar value that is the minimum value among upper range values collected. For example, the respective sample scalar values collected while repeatedly carrying out the process of step S303 will include lower intensity values and upper (high) intensity values as samples are taken along the X axis as the device model 102 is rotated around the Z axis. The metric is the upper intensity values, and according to some embodiments, the computing system 500 selects the minimum value of the upper range values as the Z-rotation angle in step S305. For example, a value may be collected (in step S303) for each degree. Then, the computing system 500 selects from those 180 values (e.g., 180 respective values for each degree at which a sample scalar value is collected) the one that has the minimum value among those values which are upper (high) intensity values. The Z-rotation angle is the angle at which the device model 102 surface is most likely aligned with the skin surface.

In steps S306 to S309, a process is carried out that is similar to that described with reference to S302 to S305, except that rotation is around the X axis (see step S306) and the sample scalar value is obtained along the Z axis for each incremental degree of rotation around the X axis. Thus, in step S306, the resulting device model is subsequently rotated about a second axis that is orthogonal to the first rotation axis and parallel to the surface of the device model after the first axis rotation. In step S307, at a set of points on the device model surface are sampled in the same way as at a geometry that is perpendicular to the second rotation axis. In step S308, it is determined whether steps S306 and S307 have been performed for each angle of the 180 degrees. Then, in step S309, the optimal value determines the second rotation angle.

In some embodiments, in step S306, the computing system 500 rotates the device model around the X axis. For example, the computing system 500 may rotate the device model around the X axis shown in FIG. 1. The device model 102 is rotated about the X axis passing through the insertion point.

In step S307, the computing system 500 samples scalar values along the Z axis. In step S308, the computing system 500 determines whether the device model has been rotated 180 degrees. If not (No in step S308), the process returns to step S306 and the process S306-S308 is repeated. Accordingly, for each angle as the device model 102 is rotated, samples of the underlying image data values are collected for different angle positions at a set of points that correspond to the device model surface at a geometry that is perpendicular to the rotation axis. The amount of sample scalar values collected is based on the desired resolution. For example, in some embodiments the process S306-S308 is repeated for every one degree for a total of 180 sample scalar values. For each angle, multiple points in the image are sampled, each point corresponding to a voxel of the image. A sample scalar value is obtained along the Z axis for each incremental degree of rotation around the X axis. When the computing system 500 determines that the device model has been rotated 180 degrees and all sample scalar values have been collected for each sampled angle (Yes in step S308), then the process advances to step S309.

In step S309, a metric to be optimized is calculated for the point sample values at each angle, such as the range, gradient or a combination thereof, that can be specific to the imaging modality, and the optimal value determines the second device model rotation angle. The device model rotation angle selected in step S309 may be the angle which corresponds to a sampled scalar value that is the minimum value among upper range values collected. For example, the respective sample scalar values collected while repeatedly carrying out the process of step S307 will include lower intensity values and upper (high) intensity values as samples are taken along the Z axis as the device model is rotated around the X axis. The metric is the upper intensity values, and according to some embodiments, the computing system 500 selects the minimum value of the upper range values as the X-rotation angle in step S309. For example, a value may be collected (in step S307) for each degree. Then, the computing system 500 selects from those 180 values (e.g., 180 respective values for each degree at which a sample scalar value is collected) the one that has the minimum value among those values which are upper (high) intensity values. The X-rotation angle is the angle at which the device model surface is most likely aligned with the skin surface.

The resulting device model after applying the two rotations (e.g., along the Z axis and the X axis) is expected to roughly conform to the patient skin surface orientation, but additional iterations can be performed using new axes of the resulting device model. In step S310, the computing system 500 checks whether the device model may be flipped 180 degrees, for which samples of image data values on either side of the resulting surface plane are taken. In step S311, the computing system 500 determines whether it is necessary to flip the device model resulting from the above-described process. If it is necessary to flip the device model (Yes in step S311), then in step S312, the device model is flipped and the process of algorithm 300 ends. On the other hand, if it is not necessary to flip the device model (No in step S311), the process of algorithm 300 ends without flipping the device model. Regarding step S310, the computing system 500 samples image data values along the Y axis, which is the vertical axis of the cone. The computing system 500 samples voxel values along the Y axis on both sides of the device model plane. The higher intensity values represent those voxels inside the medical image, while lower intensity values represent voxels outside. For example, if positive (+) Y values have high intensity values, then it is determined that the device model needs to be flipped because the positive (+) Y values should be above the skin plane outside the medical image, which region has low intensity values. On the other hand, if negative (−) Y values have high intensity values, then it is determined that the device model does not need to be flipped because the negative (−) Y values are below the skin plane inside the medical image region, which region should have high intensity values. In other words, the device model is correctly oriented relative to the patient anatomy when the negative (−) Y values have high intensity values.

In some embodiments, the two rotation steps (S302 and S306) can be performed simultaneously and the image sampled not only along a single device axis but at a chosen combination of points on the device base plane or surface.

By virtue of carrying out the algorithm 300 of FIG. 3, the virtual device model has been registered to the image space automatically and the most likely configuration of the device on the skin surface has been approximated before the actual device is placed on the patient. The virtual model of the device and its reachable area are overlaid (as shown in 103 of FIG. 1) on the planning image data, in order to visualize and quantify the reachability of the target. For example, in some embodiments, following the process of FIG. 3, an image (such as the image illustrated at item 103 of FIG. 1) is presented in a GUI on a display. However, the information about device orientation and reachability of the target may be output in any suitable manner including, for example, as textual and/or numerical information, rather than or in addition to graphical information.

In some embodiments, where there are multiple options for placement of the device relative to the insertion point, the algorithm may execute iteratively for different possible device locations and compute a metric for reachability, for example the proximity to the edge of the reach zone, that can help evaluate a preferred device placement.

According to the above-described features of the present disclosure, the systems and methods disclosed herein provide increased confidence before mounting the device on whether the target can be reached from the chosen insertion point using the device. Thus, the present disclosure provides systems and methods which reduce procedure time; avoid remounting steps; and enable better planning with good consistency between model and device. The systems and methods disclosed herein provide simplicity which avoids other more complex techniques that can be envisioned using skin segmentation, which reduces the need for computational resources. Moreover, automatically positioning the device allows ease of use and reduced time for planning, as no additional input is required from the user. Furthermore, the systems and methods of the present disclosure reduce computational time and allow greater compatibility with different devices.

Figure 4:
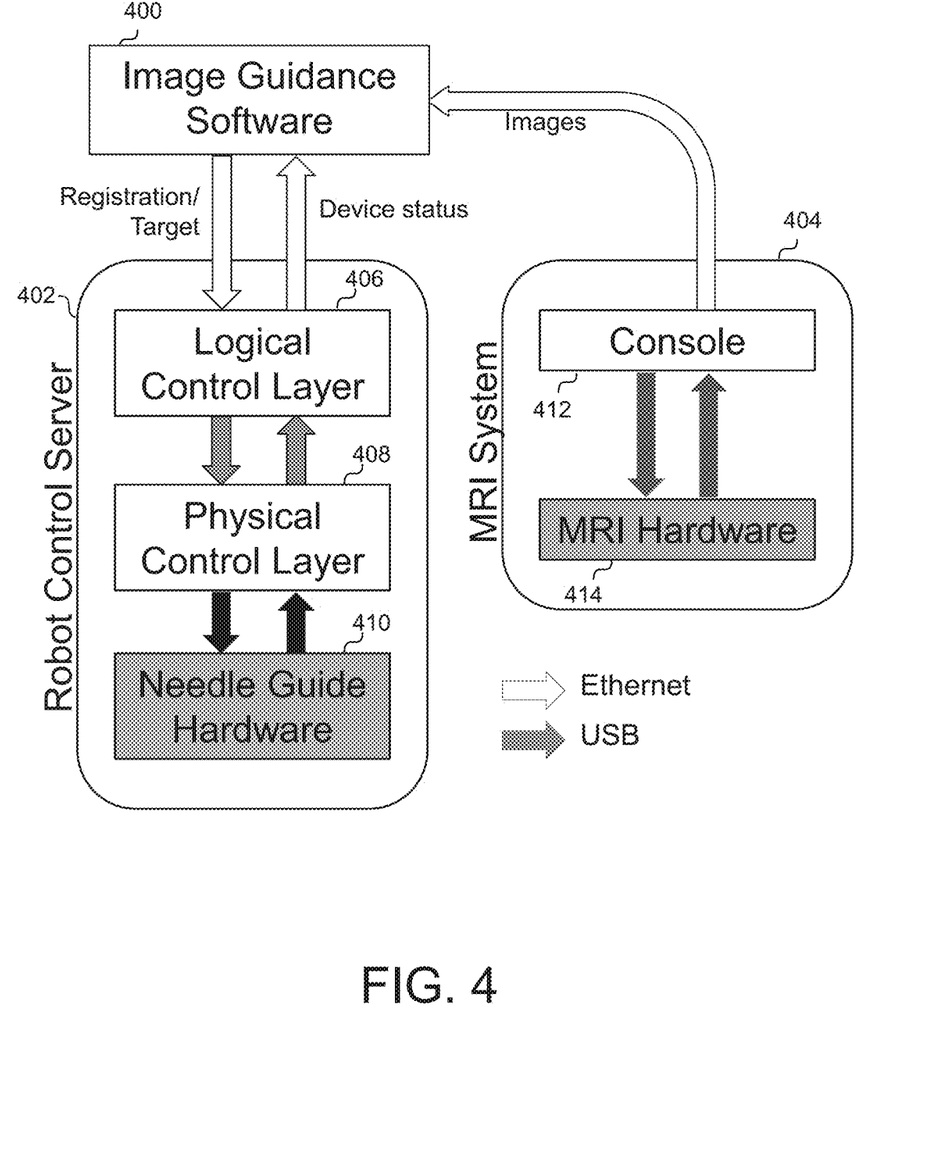
FIG. 4 illustrates an example system diagram of a needle guide robot system including image guidance software, robot control server of a needle guide robot, and MRI system including an MRI scanner in accordance with some embodiments.

FIG. 4 illustrates an example system diagram of a needle guide robot system including image guidance software, robot control server of a needle guide robot, and MRI system including an MRI scanner in accordance with some embodiments. FIG. 4 represents one example of a needle guide system, but the present disclosure is not limited to such a system. For example, according to some embodiments, the needle guide device is a manually operated device. For example, needle guide devices that may be used in combination with systems described herein are described in U.S. Pat. No. 9,222,996 and in U.S. patent application Ser. No. 15/808,703, both of which are herein incorporated by reference in their entirety. Any suitable needle guide device may be used in conjunction with the embodiments of the present disclosure. The following description of FIG. 4 is merely an example of a needle guide system which may be used in conjunction with the systems and methods described herein.

Robot Control Software

In some embodiments, a software system is provided that has three layers of components including, image guidance software 400, logical control layer 406, and physical control interface 408 (FIG. 4). Those components are implemented as independent software processes, and communicate with each other via, for example, Ethernet and Universal Serial Bus (USB). However, in other embodiments, two more of these components are integrated into a single software process.

The details of those three components are as follows:

Image Guidance Software

The image guidance software 400 is the top layer component in the system and is exemplified in FIG. 4. The image guidance software 400 works, for example, as a primary user interface for the physician and/or operator. It is implemented as described herein as a plug-in module for 3D Slicer, open-source medical image computing software and, through this or other software, receives images from the MRI System 404 which includes the console 412 and MRI hardware 414, which includes an MRI scanner. The image guidance software 400 assists the physician in performing the following tasks.

Needle Placement Planning.

The physician can define a trajectory of needle placement by specifying the targets and skin entry point on the planning image. The software displays a section of the planning image along any plane and allows the physician to specify the points by clicking on it with a mouse. Once the trajectory has been defined, it can re-slice the 3D image with a plane along the trajectory so that the physician can find any critical structures and obstacles around the path (see FIG. 1). The defined trajectory is transferred to the robot control server 402. The final decision to move the actuator, however, may be made by the physician standing by the gantry; the actuators can be powered on when the physician presses down a footswitch.

Device-to-Image Registration.

The software can automatically register the needle guide device to the image coordinate system. A registered device model is overlaid on the planning image data and its accessible range is presented on the image, so that the operator can confirm that the all targets are in range (see FIG. 1, item 103). Information is transferred to the robot control server 402 over the network using, for example, the OpenIGTLink protocol.

Monitoring and Confirmation of Probe Placement.

The software can be used to visualize the current position and orientation of the device with a 3D model overlaid on the images during planning for or performance of a procedure. In addition, it also can display confirmation images that show the probe inserted into the patient with the planned trajectory and target (see FIG. 1). Those features allow the physicians to monitor the device and confirm the probe placement.

Logical Control Layer

The Logical Control Layer (LCL) 406 sits in the middle layer of the system and interfaces the image guidance software 400 and low-level physical control layer (PCL) 408. This layer of the robot control server 402 can encapsulate the hardware and the kinematic structure of the device, and provide a device-independent application program interface (API) to the upper layer. Therefore, the LCL 406 consists of the following subcomponents:

TCP/IP Network Interface to the Upper Layer.

Through this interface, the LCL 406 receives commands to the hardware from the upper layer including the target position, and provides the current status of the hardware (410) to the upper layer including the current position of the needle guide, and the status of the device. It also provides the required needle insertion depth as a result of kinematics computation (see Kinematics engine below) to the upper layer. In some embodiments, the network interface is compliant with the OpenIGTLink protocol, and thus it can communicate with software compatible with OpenIGTLink.

Kinematics Engine.

In some embodiments, the hardware-independent commands received from the upper layer are translated into the target positions of individual actuators based on the kinematics of the needle guide device, and sent to the PCL 408. Moreover, in some embodiments, current positions of individual actuators received from the PCL 408 are translated to the position and orientation of the needle guide and sent to the upper layer. According to some embodiments, the needle guide device is a manually operated device.

Serial Interface to the Lower Layer.

The LCL 406 communicates with the lower layer subcomponent through a universal serial bus (USB). Through this exemplary interface, target positions of individual actuators and other device-specific commands are sent to the PCL 408, while the current status of the device and the encoder readings of individual actuators are sent to the image guidance software 400. The information exchanged through this interface is dependent on the kinematic structure, but independent from the physical hardware (e.g. motor drivers and encoders).

Physical Control Layer

The role of the Physical Control Layer (PCL) 408 is to provide an interface that is independent from the physical input/output (I/O), but dependent on the kinematic structure. In some embodiments, the PCL 408 runs on a Linux-based embedded computer equipped with a USB interface for the communication with the LCL 406, and a digital input/output interface for reading inputs from encoders and footswitch and giving the target speeds of individual motors to the motor drivers. Once the controller receives target positions for individual actuators, it performs closed-loop PID control of individual motors. Throughout this process, the PCL 408 can optionally keep sending current positions and other device status.

Computing System

FIG. 5 illustrates an example computing system 500. In some embodiments, the computing system 500 includes the image guidance software described herein. For example, in some embodiments, the computing system 500 may include the image guidance software 400 of FIG. 4. The various programs and data—for example, software modules, libraries, tools, user interface elements, or other components—of the image guidance software reside in the computing system 500 in any suitable manner, in accordance with various embodiments. For example, these components may reside in one or multiple storage locations. The components of the image guidance software may be provided as part(s) of a single software application or as a plurality of stand-alone software applications. The computing system 500 provides access to the image guidance software. In some embodiments, the image guidance software executing on the computing system 500 performs one or more steps of one or more methods described or illustrated herein, or provides functionality described or illustrated herein. For example, programs of the image guidance software may include instructions that, when executed by one or more processors, cause the computing system 500 to perform the process described with reference to FIG. 3.

The term computing system as used herein includes but is not limited to one or more software modules, one or more hardware modules, one or more firmware modules, or combinations thereof, that work together to perform operations on electronic data. The physical layout of the modules may vary. A computing system may include multiple computing devices coupled via a network. A computing system may include a single computing device where internal modules (such as a memory and processor) work together to perform operations on electronic data. In some embodiments, a single computing system 500 includes the image guidance software.

In some embodiments, the image guidance software executing on the computing system 500 interacts with the robot control server 402 and with the MRI System 404. The computing system 500 may use any suitable protocol(s), standard(s), data exchange format(s), or combination(s) of these, to communicate with and send/receive information to/from one or more of the systems described herein. The computing system 500 may send and receive information and requests using OpenIGTLink. The computing system 500 can receive, send, and store DICOM (Digital Imaging and Communications in Medicine) files and data. For example, the computing system 500 may receive a medical image from the MRI System 404. Additionally, the computing system 500 may send HTTP requests and provide HTTP responses. The responses may include Hyper Text Markup Language (HTML) files, or other suitable files, executable code, such as JAVASCRIPT, form elements, images, or other content. One or more elements of the content may be stored at the computing system 500. In some embodiments, the computing system 500 uses Simple Object Access Protocol (SOAP) to receive and send messages.

The computing system 500 includes one or more processor(s) 501, memory 502, storage 503, an input/output (I/O) interface 504, a communication interface 505, and a bus 506. The computing system 500 may take any suitable physical form. For example, and not by way of limitation, the computing system 500 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, PDA, a tablet computer system, one or more servers, a workstation, or a combination of two or more of these. In some embodiments, the computing system 500 is unitary. In some embodiments, the computing system 500 is distributed. The computing system 500 may span multiple locations. The computing system 500 may span multiple machines.

The processor(s) 501 include hardware for executing instructions, such as those making up a computer program. The processor(s) 501 may retrieve the instructions from the memory 502, the storage 503, an internal register, or an internal cache. The processor(s) 501 then decode and execute the instructions. Then, the processor(s) 501 write one or more results to the memory 502, the storage 503, the internal register, or the internal cache. The processor(s) 501 may provide the processing capability to execute the operating system, programs, user and application interfaces, and any other functions of the computing system 500.

The processor(s) 501 may include a central processing unit (CPU), one or more general-purpose microprocessor(s), application-specific microprocessor(s), and/or special purpose microprocessor(s), or some combination of such processing components. The processor(s) 501 may include one or more graphics processors, video processors, audio processors and/or related chip sets.

In some embodiments, the memory 502 includes main memory for storing instructions for the processor(s) 501 to execute or data for the processor(s) 501 to operate on. By way of example, the computing system 500 may load instructions from the storage 503 or another source to the memory 502. During or after execution of the instructions, the processor(s) 501 may write one or more results (which may be intermediate or final results) to the memory 502. One or more memory buses (which may each include an address bus and a data bus) may couple the processor(s) 501 to the memory 502. One or more memory management units (MMUs) may reside between the processor(s) 501 and the memory 502 and facilitate accesses to the memory 502 requested by the processor(s) 501. The memory 502 may include one or more memories. The memory 502 may be random access memory (RAM).

The storage 503 stores data and/or instructions. As an example and not by way of limitation, the storage 503 may include a hard disk drive, a floppy disk drive, flash memory, an optical disc, a magneto-optical disc, magnetic tape, or a Universal Serial Bus (USB) drive or a combination of two or more of these. In some embodiments, the storage 503 is a removable medium. In some embodiments, the storage 503 is a fixed medium. In some embodiments, the storage 503 is internal to the computing system 500. In some embodiments, the storage 503 is external to the computing system 500. In some embodiments, the storage 503 is non-volatile, solid-state memory. In some embodiments, the storage 503 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. The storage 503 may include one or more memory devices. The storage 503 may store application data, program modules and other information. One or more program modules stored in the storage 503 are configured to cause various operations and processes described herein to be executed. In some embodiments, the image guidance software resides on the storage 503 and executes on the computing system 500. The storage 503 may further store other programs and/or drivers that enable various functions of the computing system 500, graphical user interface (GUI) functions, and/or processor functions. The storage 503 may also store data files including, for example, image data, user data, configuration information, GUI components, such as graphical elements or templates, or other data required by the computing system 500.

The I/O interface 504 includes hardware, software, or both providing one or more interfaces for communication between the computing system 500 and one or more I/O devices. In some embodiments, the computing system 500 includes one or more I/O devices. One or more of these I/O devices may enable communication between a person and the computing system 500. By way of example and not by way of limitation, an I/O device may include a keyboard, keypad, microphone, monitor, mouse, touchpad, speaker, still camera, stylus, tablet, touch screen, trackball, video camera, another suitable I/O device or a combination of two or more of these. An I/O device may include one or more sensors. In some embodiments, the I/O interface 504 includes one or more device or software drivers enabling the processor(s) 501 to drive one or more of these I/O devices. The I/O interface 504 may include one or more I/O interfaces.

In some embodiments, the computing system 500 includes a display. For example, the display may be a liquid crystal display (LCD). In some embodiments, the image guidance software running on the computing system 500 presents GUI data on the display. In some embodiments, the GUI data is presented in conjunction with medical image data. Regarding outputting signals to the display, the processor(s) 501 rasterize an image to be displayed on the display, and transfer the rasterized image to the display via the I/O interface 504. The display then displays the image, such as a GUI. The processor(s) 501 are further operable to cause other types of images, such as medical images from the MRI System 404, to be displayed on the display. The computing system 500 may receive an input signal based on user inputs at the display. For example, in some embodiments, the display includes a touch sensitive element operable to receive user inputs or commands based on the touching one or more interface elements on the display. The interface element may be a graphical object presented on the display. A user may touch the touch sensitive display with a finger, stylus, or other tool to provide a user input. When the user touches a specific region on the touch sensitive display, the processor(s) 501 are notified via the I/O interface 504 of the coordinates of the region. The processor(s) 501 determine the content of a user input based on the notified coordinates and the display contents on the display, and execute processing based on them. In some embodiments, a mouse or touchpad is used in conjunction with information presented on the display to receive user inputs and selections. For example, a cursor may be used to select one or more interface elements presented in the GUI on the display. According to various embodiments, the touch sensitive display, the cursor, or other suitable method for providing an input, is used to specify one or more location(s) on a medical image presented in the GUI on the display to indicate, for example, a target and a planned insertion point for inserting a needle into a patient.

In some embodiments, the computing system 500 includes a keyboard/keypad. User inputs may also be provided via the keyboard/keypad. When the user presses a hard key of the keyboard/keypad, the processor(s) 501 are notified via the I/O interface 504 of information indicative of the user input. The processor(s) 501 execute processing based on the notification. The hard keys and/or buttons of the keyboard/keypad may be arranged in any suitable configuration. Furthermore, the input structures may include buttons, keys, switches, control pads, or other suitable structure, depending on specific implementation requirements.

The communication interface 505 includes hardware, software, or both providing one or more interfaces for communication (such as, for example, packet-based communication) between the computing system 500 and one or more other computing systems or one or more networks. As an example and not by way of limitation, the communication interface 505 may include a network interface card (NIC) or a network controller for communicating with an Ethernet or other wire-based network or a wireless NIC (WNIC) or wireless adapter for communicating with a wireless network, such as a WI-FI network. This disclosure contemplates any suitable network and any suitable communication interface 505 for it. As an example and not by way of limitation, the computing system 500 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, the computing system 500 may communicate with a wireless PAN (WPAN) (such as, for example, a Bluetooth WPAN or an ultra-wideband (UWB) network), a WI-FI network, a WI-MAX network, a cellular telephone network (such as, for example, a Global System for Mobile Communications (GSM) network), or other suitable wireless network or a combination of two or more of these. The computing system 500 may include any suitable communication interface 505 for any of these networks, where appropriate. The communication interface 505 may include one or more communication interfaces 505.

The bus 506 interconnects various components of the computing system 500 thereby enabling the transmission of data and execution of various processes. The bus 506 may include one or more types of bus structures including a memory bus or memory controller, a peripheral bus, and a local bus using any of a variety of bus architectures.

The above description serves to explain principles of the present disclosure; but the present disclosure should not be limited to the examples described above. For example, the order and/or timing of some of the various operations may vary from the examples given above without departing from the scope of the present disclosure. Further by way of example, the type of network and/or computing systems may vary from the examples given above without departing from the scope of the present disclosure. Other variations from the examples given above may also exist without departing from the scope of the present disclosure. While particular examples of GUIs are illustrated, it will be understood that various other implementations of GUIs are within the scope of the present disclosure. For example, various features of the illustrated examples could be modified, rearranged, or removed, or one or more features could be added without departing from the scope of the present disclosure.

The scope of the present disclosure includes a computer-readable medium storing instructions that, when executed by one or more processors, cause the one or more processors to perform one or more embodiments described herein. Examples of a computer-readable medium include a hard disk, a floppy disk, a magneto-optical disk (MO), a compact-disk read-only memory (CD-ROM), a compact disk recordable (CD-R), a CD-Rewritable (CD-RW), a digital versatile disk ROM (DVD-ROM), a DVD-RAM, a DVD-RW, a DVD+RW, magnetic tape, a nonvolatile memory card, and a ROM. Computer-executable instructions can also be supplied to the computer-readable storage medium by being downloaded via a network.

While the present disclosure has been described with reference to exemplary embodiments, it is to be understood that the present disclosure is not limited to the exemplary embodiments described.

What is claimed is:

1. A method comprising:
    obtaining image data of a subject;
    obtaining information indicating a planned insertion point on the image data for performing a medical procedure using a needle guide device to guide a medical device;
    determining a planned needle trajectory for performing the medical procedure, the planned needle trajectory based on the planned insertion point and a target within the image data;
    determining an orientation of the needle guide device based on the planned insertion point and the planned needle trajectory;
    determining whether the target is within a reachable range of the medical device using the needle guide device; and
    outputting information indicating whether the target is within the reachable range of the medical device based on the orientation of the needle guide device.

2. The method of claim 1, wherein determining the orientation of the needle guide device includes pivoting a model of the needle guide device around the planned needle insertion point.

3. The method of claim 1, wherein determining the orientation of the needle guide device includes computing a metric related to a correspondence between a skin plane and a bottom surface of the needle guide device.

4. The method of claim 3, wherein computing the metric includes:
    sampling a plurality of points along a path in the image data,
    computing a gradient of scan values in neighborhoods of such points, and
    determining such points for which such gradient includes a sharp change in value as being on or near an exterior surface of the subject.

5. The method of claim 1, wherein outputting information indicating the reachability of the target based on the orientation of the needle guide device includes:
    determining a distance between a boundary of a reachable area of a needle to be guided by the needle guide device, and
    providing an indication of such distance to a user for determining whether the determined distance would provide sufficient headroom for usage of the needle guide device.

6. A system comprising:
    one or more processors; and
    memory storing executable instructions, which when executed by the one or more processors, cause the system to:
    obtain image data of a subject;
    obtain information indicating a planned insertion point on the image data for performing a medical procedure using a needle guide device to guide a medical device;
    determine a planned needle trajectory for performing the medical procedure, the planned needle trajectory based on the planned insertion point and a target within the image data;
    determine an orientation of the needle guide device based on the planned insertion point and the planned needle trajectory;
    determine whether the target is within a reachable range of the medical device using the needle guide device; and
    output information indicating whether the target is within the reachable range of the medical device based on the orientation of the needle guide device.

7. A computer-readable storage medium storing executable program instructions, which when executed by a computing system with one or more processors, cause the computing system to:
    obtain image data of a subject;
    obtain information indicating a planned insertion point on the image data for performing a medical procedure using a needle guide device;
    determine a planned needle trajectory for performing the medical procedure, the planned needle trajectory based on the planned insertion point and a target within the image data;
    determine an orientation of the needle guide device based on the planned insertion point and the planned needle trajectory;
    determine whether the target is within a reachable range of the medical device using the needle guide device; and
    indicating whether the target is within the reachable range of the medical device based on the orientation of the needle guide device.

8. The method of claim 1, further comprising computing a reachability metric for determining the reachable range of the target.

9. The method of claim 1, wherein outputting information indicating the reachability of the target based on the orientation of the needle guide device includes displaying the reachable range as a circular segment or arc shape on a display.

10. The method of claim 1, wherein outputting information indicating the reachable range of the target based on the orientation of the needle guide device includes displaying the reachability conically on a display.

11. The method of claim 1, wherein the medical device is a needle.

12. The method of claim 1, wherein the medical device is an ablation probe.

* * * * *